United States Patent
Lecocq et al.

(10) Patent No.: US 6,911,410 B2
(45) Date of Patent: Jun. 28, 2005

(54) CATALYST COMPOSITION CONTAINING AN ALUMINOXANE FOR DIMERIZING, CO-DIMERIZING AND OLIGOMERIZING OLEFINS

(75) Inventors: Vincent Lecocq, Paris (FR); Hélène Olivier-Bourbigou, Rueil Malmaison (FR)

(73) Assignee: Institut Francais Du Petrole, Rueil Malmaison (FR)

( * ) Notice: Subject to any disclaimer, the term of this patent is extended or adjusted under 35 U.S.C. 154(b) by 158 days.

(21) Appl. No.: 10/356,741

(22) Filed: Feb. 3, 2003

(65) Prior Publication Data

US 2003/0181775 A1 Sep. 25, 2003

(30) Foreign Application Priority Data

Feb. 4, 2002 (FR) ............................................ 02 01254

(51) Int. Cl.[7] .............................................. B01J 31/00
(52) U.S. Cl. ...................... 502/150; 502/103; 502/113; 502/117; 502/121; 502/123; 502/124; 502/164; 526/139
(58) Field of Search ................................ 502/150, 103, 502/113, 117, 121, 123, 124, 164, 139

(56) References Cited

U.S. PATENT DOCUMENTS

| | | | | |
|---|---|---|---|---|
| 5,104,840 A | | 4/1992 | Chauvin et al. | |
| 5,892,124 A | * | 4/1999 | Olivier et al. | 568/324 |
| 6,103,908 A | * | 8/2000 | Bahrmann et al. | 546/347 |
| 6,114,272 A | * | 9/2000 | Bahrmann | 502/164 |
| 6,139,723 A | * | 10/2000 | Pelrine et al. | 208/422 |
| 6,365,301 B1 | * | 4/2002 | Michot et al. | 429/307 |
| 6,395,948 B1 | * | 5/2002 | Hope et al. | 585/510 |
| 6,472,565 B1 | * | 10/2002 | Bahrmann et al. | 568/454 |
| 6,501,001 B2 | * | 12/2002 | Commereuc et al. | 585/514 |
| 6,573,405 B1 | * | 6/2003 | Abbott et al. | 564/292 |
| 6,696,532 B2 | * | 2/2004 | Cavell et al. | 526/131 |
| 6,703,507 B2 | * | 3/2004 | Bahrmann et al. | 546/24 |
| 2001/0049398 A1 | | 12/2001 | Olivier-Bourbigou et al. | |
| 2003/0109766 A1 | | 6/2003 | Commereuc et al. | |

FOREIGN PATENT DOCUMENTS

| | | |
|---|---|---|
| FR | 2804622 | 8/2001 |
| FR | 2806644 | 9/2001 |
| WO | WO 0181436 | 11/2001 |

* cited by examiner

*Primary Examiner*—J. A. Lorengo
*Assistant Examiner*—Jennine Brown
(74) *Attorney, Agent, or Firm*—Millen White Zelano & Branigan, P.C.

(57) ABSTRACT

A catalyst composition for use in dimerizing, co-dimerizing or oligomerizing olefins results from dissolving a nickel compound, optionally mixed or complexed with a ligand, in a medium resulting from mixing:

at least one quaternary ammonium halide and/or at least one quaternary phosphonium halide;
at least one aluminum halide;
and at least one aluminoxane.

24 Claims, No Drawings

CATALYST COMPOSITION CONTAINING AN ALUMINOXANE FOR DIMERIZING, CO-DIMERIZING AND OLIGOMERIZING OLEFINS

BACKGROUND OF THE INVENTION

1. Field of the Invention

The present invention relates to the field of dimerizing, co-dimerizing and oligomerizing olefins. More particularly, it concerns an improved catalyst composition for use in those reactions.

2. Description of the Prior Art

French Patent No. 2,611,700 describes the use of liquids with an ionic nature formed from aluminum halides and quaternary ammonium halides as solvents for organometallic nickel complexes for catalyzing olefin dimerization. The use of such media, which are not miscible with aliphatic hydrocarbons, in particular with olefin dimerization products, allows better use of homogeneous catalysts.

U.S. Pat. No. 5,104,840 describes a liquid composition with an ionic nature resulting from contacting quaternary ammonium halides and/or quaternary phosphonium halides with alkyl aluminum dihalides and an optional aluminum trihalide. That patent also describes the use of such media as solvents for transition metal complexes, in particular nickel complexes containing no nickel-carbon bond, which are transformed into catalysts for oligomerizing olefins. In the present text, these media will be termed "molten salts" as they are liquid at moderate temperatures.

That work shows that the most active and most stable nickel catalysts are obtained in "molten salts" constituted by one molar equivalent of ammonium halide and/or phosphonium halide with one equivalent and more of an aluminum trihalide, and optionally any quantity of an alkylaluminum dihalide. That formulation has been shown to be of particular advantage as the nickel complexes dissolved therein have a high catalytic activity.

SUMMARY OF THE INVENTION

It has now been discovered that the alkylaluminum dihalide can be replaced by an aluminoxane. This results in an improvement in the activity of the reaction and better retention of the constituents of the catalytic system in the ionic liquid.

Thus, the invention provides a catalyst composition comprising at least one nickel compound, optionally mixed or complexed with a phosphorus-containing or nitrogen-containing ligand, at least partially dissolved in a non aqueous medium with an ionic nature ("molten salt" type medium), resulting from bringing at least one aluminum halide (product B) into contact with at least one quaternary ammonium halide and/or at least one quaternary phosphonium halide (product A) and at least one aluminoxane (product C).

DETAILED DESCRIPTION OF THE INVENTION

The "molten salt" type medium in which the nickel compound is dissolved, optionally mixed or completed with a phosphorus-containing or nitrogen-containing ligand, is constituted by a mixture of:

a) at least one quaternary ammonium and/or quaternary phosphonium halide, more particularly a chloride and/or or bromide (product A);

b) at least one aluminum halide (product B); and c) at least one aluminoxane (product C).

Quaternary ammonium halides and quaternary phosphonium halides (product A) that can be used in the context of the invention preferably have general formulae $NR^1R^2R^3R^4X$ and $PR^1R^2R^3R^4X$, in which X represents Cl or Br, $R^1$, $R^2$, $R^3$ and $R^4$, which may be identical or different, each represent hydrogen, or an aliphatic (saturated or unsaturated) or aromatic hydrocarbon group containing 1 to 12 carbon atoms. The quaternary ammonium and/or phosphonium halides can also be derived from heterocycles containing 1, 2 or 3 nitrogen and/or phosphorus atoms. Examples that can be cited are tetrabutylphosphonium chloride, N-butylpyridinium chloride, ethylpyridinium bromide, 3-butyl-1-methyl imidazolium chloride, diethylpyrazolium chloride, pyridinium hydrochloride and trimethylphenylammonium chloride.

The aluminum halides used as products B in accordance with the invention are preferably the aluminum chloride or bromide.

The aluminoxanes used in accordance with the invention (product C) are usually alkyl aluminoxanes (or their modified formulae) in which the alkyl group can comprise 1 to 6 carbon atoms, or alkyl aluminoxane halides or aryl aluminoxanes. Non limiting examples that can be cited are methyl aluminoxane, ethyl aluminoxane, isobutyl aluminoxane and tert-butyl aluminoxane. These aluminoxanes can contain free or complexed trialkylaluminum.

The components of the "molten salts" as defined above are generally employed in mole ratios A:B of 1:0.5 to 1:3, preferably 1:1 to 1:2; product C is employed in a mole ratio with product B of at most 100:1, preferably 0.005:1 to 10:1. However, the components and their proportions must be such that the mixture is liquid at the temperature at which the nickel compound is introduced, optionally complexed or mixed with a phosphorus-containing or nitrogen-containing ligand, although the catalytic dimerization reaction can be carried out at a temperature that is lower or higher than the melting temperature of the catalyst composition.

Examples of the nickel compounds used in the catalyst compositions of the invention are the chloride, bromide, sulfate, carboxylates (for example 2-ethylhexanoate), phenolates and acetylacetonate. It is also possible to use organometallic nickel complexes as well as zero-valent nickel complexes such as nickel bis(cycloocta-1,3-diene), nickel bis(cyclooctatetraene), nickel bis (cycloocta-1,3,7-triene), bis(o-tolylphosphito)nickel(ethylene), nickel tetrakis (triphenylphosphite) and nickel bis(ethylene).

Examples of nickel compounds that can be used in the constitution of the catalyst compositions of the invention and carrying a phosphorus-containing or nitrogen-containing ligand that can be cited include the following:

[$NiCl_2$, 2(pyridine)];

[$NiCl_2$, 2P(2-dicyclopentylethyl-4-pyridine)]$_2$ chloride;

[$NiCl_2$, 2P (2-dicyclopentylethyl-N-ethylpyridinium tetrafluoroborate)]$_2$;

π-allyl-nickel-2-dicyclopentylphosphinoethyl-4-pyridine;

[$NiCl_2$, acenaphthyl-bis(4-trifluoromethylphenylimine)];

[$NiCl_2$, glyoxal-bis(2,6-dimethylphenylimine)]; and

[$NiCl_2$, diacetyl-bis(2,6-diisopropylphenylimine)].

The phosphorus-containing ligands used in accordance with the invention mixed or complexed with nickel can be selected from:

phosphines with general formulae:

$PR'_1R'_2R'_3$ and $R'_1R'_2P-R'-PR'_1R'_2$ in which R'₁, R'₂ and R'₃, which may be identical or different, are alkyl, cycloalkyl, aryl or aralkyl radicals containing 1 to 10 carbon atoms; and phosphites with general formulae:

P(OR"₁)(OR"₂)(OR"₃) and (—O—R"₅—O—)P(OR"₂)

in which R"₁, R"₂, R"₃, and R"₅, which may be identical or different, are aryl or aralkyl radicals.

These phosphines and phosphates can also carry a function such as an amine, ammonium, alcohol, carboxylic acid, ester, sulfonate, phosphonium or phosphonate function.

Functional phosphines carrying a substituent that can be used are 2-dicyclopentylphosphinoethyl-4-pyridine, 2-dicyclopentylphosphinoethyl-2-pyridine, 2-diisobutylphosphinoethyl-4-pyridine, 2-diisopropylphosphinoethyl-4-pyridine and their pyridine quaternization derivatives, 2-dicyclopentylphosphinoethyl-N-imidazole, 2-diisopropylphosphinoethyl-N-imidazole, 2-diisobutylphosphinoethyl-N-imidazole and their imidazole quaterization derivatives.

The nitrogen-containing ligands of the invention are preferably selected from the group formed by mono-amines, di, tri- and poly-amines, imines, di-imines, pyridine and substituted pyridines, bipyridine, imidazole and substituted imidazoles, pyrrole and substituted pyrroles, pyrazole and substituted pyrazoles.

Particular examples of nitrogen-containing diimine type ligands have general fomula:

R¹-N=CR₂-CR₃=N-R₄ in which R₁ and R₄, which may be identical or different, each represent a hydrocarbyl group containing 1 to 12 carbon atoms, for example an alkyl group, a saturated or unsaturated group, a cycloalkyl or aromatic, aryl or aralkyl group containing 1 to 12 carbon atoms, and R₂ and R₃, which may be identical or different, each represent hydrogen or a hydrocarbyl residue defined as R₁ and R₄.

The following developed formulae illustrate some of these products:

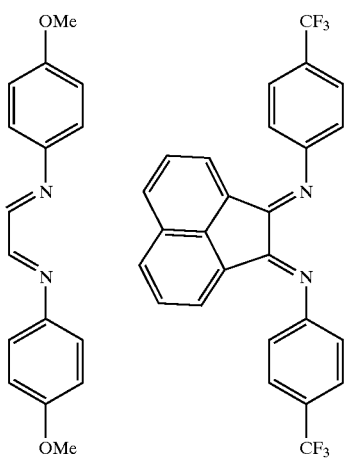

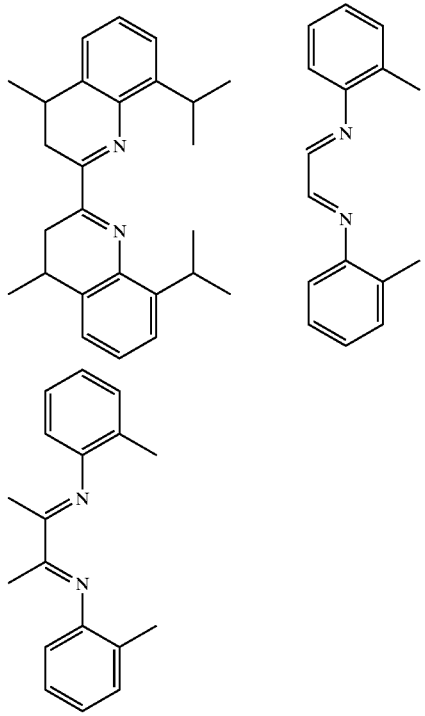

The compounds used in the catalyst composition of the invention can be mixed in any order. Mixing can be achieved by simple contact followed by stirring until a homogeneous liquid is formed. Mixing can be carried out outside the dimerization or oligomerization reactor or, as is preferable, in the reactor.

More particular olefins that can be dimerized, co-dimerized or oligomerized and in some circumstances polymerized by the catalyst compositions of the invention are ethylene, propylene, n-butenes and n-pentenes, used alone or as a mixture (co-dimerization), pure or diluted by an alkane, such as those found in cuts from oil refining processes such as catalytic cracking or steam cracking.

The catalytic olefin dimerization or oligomerization reaction or polymerization reaction can be carried out in a closed, semi-open or continuous system, with one or more reaction stages. Vigorous stirring ensures good contact between the reactant or reactants and the catalyst mixture. The reaction temperature can be from −40° C. to +70° C., preferably −20° C. to +50° C. to operate above or below the medium melting temperature, the dispersed solid state not being a limitation on the reaction taking its proper course. The heat released by the reaction can be eliminated by any means that is known to the skilled person. The pressure can be from atmospheric pressure to 20 MPa, preferably from atmospheric pressure to 5 MPa. The reaction products and the reactant or reactants which have not reacted are separated from the catalytic system by simple decanting, then fractionated.

EXAMPLES

The following examples illustrate the invention without limiting its scope. The following abbreviations are used n the examples:

BMIC: 1-butyl-3-methylimidazolium chloride;
MAO: methylaluminoxane

Example 1

Preparation of Ionic Liquid

At ambient temperature, 7 g (40 mmole) of 1-butyl-3-methyl imidazolium chloride (BMIC) and 6.53 g (48.9 mmole) of aluminum chloride (AlCl$_3$) were mixed. The mixture was liquid at ambient temperature 6.25 g of this liquid, to which 1.23 ml of a solution of methylaluminoxane in toluene containing 3 mmole of aluminum had been added, was removed.

Example 2

Butene Dimerization

A two-stage glass reactor separated by a decanter tube provided with a temperature sensor, a magnetic stirrer in the lower stage (20 ml volume) to ensure good stirring and a jacket for circulating a cooling liquid, was purged of air and moisture and maintained under 1-butene at atmospheric pressure 0.2 mmole of the NiCl$_2$, 2 pyridine complex was introduced then the temperature was reduced to 10° C. and the liquid composition as prepared above containing aluminoxane (Example 1) and 40 ml of heptane was injected using a syringe. Stirring was commenced and immediately, butene absorption was observed. When the upper, non-stirred, stage was full of liquid, the major portion of the hydrocarbon phase had been extracted. The reaction was stopped after 7 hours 35 minutes (5 extractions). At that moment, 27 kg of products per gram of Ni had been produced. An analysis of the different fractions showed that they were composed of at least 98% dimers.

After slopping stirring overnight (the reactor was kept at 10° C.), the reaction could be recommenced by recommencing stirring. The reaction was stopped after 7 hours 57 minutes on the second day and produced a further 29 kg of products per gram of nickel (3.6 kg/g Ni.h) with a selectivity for dimers that was identical to that of the first day.

The ionic liquid that served for the reaction was neutralized with dilute nitric acid and the nickel and aluminum were assayed using X ray fluorescence. Of the 11.74 mg of nickel metal introduced initially into the reaction, 10.4 mg was recovered and of the 0.61 g of aluminum (total introduced initially), 0.6 g was recovered. No extracted aluminum could be detected in the organic phase.

Examples 3 (Comparative)

The ionic liquid was prepared as described in Example 1. from 7 g (40 mmoles) of BMIC and 6.53 g (48.9 mmole) of AlCl$_3$ 6.13 g of this liquid mixture to which 1.87 mmole of ethyl aluminum dichloride had been added was removed.

The procedure was then as described in Example 2 with 0.2 mmole of nickel. The reaction was stopped after 8 hours 10 minutes. At that time, 8.5 kg of products per gram of Ni had been produced. An analysis of the different fractions showed that they were composed of 97% to 98% dimers.

Example 4

Ethylene Oligomerization

An ionic liquid was prepared from 5.58 g (32 mmole) of BMIC and 4.27 g (32 mmole) of AlCl$_3$. 2.4 ml of a solution of MAO (4 mmole) was partially dissolved therein and injected into a Grignard type reactor that had been evacuated for 4 hours at 90° C., then cooled under ethylene. A solution of the complex acenaphthyl-bis(4-trifluoromethylphenylimine) NiCl$_2$ (12 mg, 0.02 mmole; Al/Ni=200) in the remaining molten salt was then added using a syringe. The reactor was then placed under ethylene (2.5 MPa) and the solution was stirred (750 rpm) for 30 minutes at ambient temperature. The gas phase was measured and then recovered in a tank. The reactor was opened; the organic phase was transferred under argon and quenched with an aqueous acid solution. 660 mg of product was distilled from the molten salt. The total mass of the product was 24 g (20400 g of oligomers/g Ni), distributed as follows: C$_4$: 64% (of which 41% of 1-butene), C$_6$: 31% (of which 70% of 1-hexene), C$_8$: 4% (of which 3%) of 1-octene), C$_{10}$: 0.4%.

Example 5

Ethylene Oligomerization

An ionic liquid was prepared from 5.58 g (32 mmole) of BMIC and 4.27 g (32 mmole) of AlCl$_3$. 2.4 ml of a solution of MAO (4 mmole, Al/Ni=200) was partially dissolved therein and injected into a Grignard type reactor that had been evacuated for 4 hours at 90° C., then cooled under ethylene. A solution of the NiCl$_2$, 2 pyridine complex (6 mg, 0.02 mmole;) in the remaining molten salt was then added using a syringe. The reactor was then placed under ethylene (2.5 MPa) and the solution was stirred (750 rpm) for 30 minutes at ambient temperature. The gas phase was measured and then recovered in a tank. The reactor was opened; the organic phase was transferred under argon and quenched with an aqueous acid solution. The molten salt was distilled to recover the remaining product. The total mass of the product was 40 g (34000 g of oligomers/g Ni), distributed as follows: C$_4$: 66% (of which 27% of 1-butene), C$_6$: 31% (of which 4% of 1-hexene), C$_8$: 3% (of which 3% of 1-octene).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 02/01254, filed Feb. 4, 2002, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalyst composition for dimerizing, co-dimerizing and oligomerizing olefins, characterized in that it results from dissolving a nickel compound in a medium resulting from mixing:
   at least one quaternary ammonium halide and/or at least one quaternary phosphonium halide, termed product A;
   at least one aluminum halide, termed product B; and
   at least one aluminoxane, termed product C.

2. A catalyst composition according to claim 1, characterized in that the quaternary ammonium halide and quaternary phosphonium halide termed product A:
   has one of general formulae:

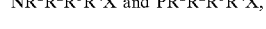

in which X represents Cl or Br, $R^1$, $R^2$, $R^3$ and $R^4$, which may be identical or different, each represents hydrogen, an aliphatic, saturated or unsaturated or aromatic hydrocarbon group containing 1 to 12 carbon atoms; or
   is derived from a heterocycle containing 1, 2 or 3 nitrogen and/or phosphorus atoms.

3. A catalyst composition according to claim 2, characterized in that product A is selected from tetrabutylphosphonium chloride, N-butylpyridinium chloride, ethyl pyridinium bromide, 3-butyl-1-methyl imidazolium chloride, diethylpyrazolium chloride, pyridinium hydrochloride and trimethylphenylammonium chloride.

4. A catalyst composition according to claim 1, characterized in that the aluminum halide used as product B is aluminum chloride or bromide.

5. A catalyst composition according to claim 1, characterized in that the aluminoxane used as product C is selected from alkylaluininoxanes and alkylaluminoxane halides in which the alkyl group contains 1 to 6 carbon atoms.

6. A catalyst composition according to claim 5, characterized in that the aluminoxane is selected from methyl aluminoxane, ethyl aluminoxane, isobutyl aluminoxane and tert-butyl aluminoxane, optionally containing free or complexed trialkylaluminum.

7. A catalyst composition according to claim 1, characterized in that products A and B are employed in a mole ratio A:B of 1:0.5 to 1:3 and product C is employed in a mole ratio of at most 100:1 with product B.

8. A catalyst composition according to claim 7, characterized in that products A and B are employed in a mole ratio A:B of 1:1. to 1:2; product C is employed in a mole ratio of at most 0.005:1 to 10:1 with product B.

9. A catalyst composition according to claim 1, characterized in that the nickel compound is selected from nickel salts, organometallic nickel complexes and zero-valent nickel complexes.

10. A catalyst composition according to claim 9, characterized in that said nickel compound is selected from the chloride, bromide, sulfate, carboxylates, phenolates and acetylacetonate, nickel bis(cycloocta-1,3-diene), nickel bis (cyclooctatetraene), nickel bis (cycloocta-3,7-triene), bis(o-tolylphosphito)nickel(ethylene), nickel tetrakis (triphenylphosphite) and nickel bis(ethylene).

11. A catalyst composition according to claim 1, characterized in that said nickel compound is mixed or complexed with a phosphorus-containing or nitrogen-containing ligand.

12. A catalyst composition according to claim 1, characterized in that the nickel compound is selected from:

[NiCl$_2$, 2(pyridine)];

[NiCl$_2$, 2P(2-dicyclopentylethyl-4-pyridine)]$_2$;

[NiCl$_2$, 2P(2-dicyclopentylethyl-N-ethylpyridinium tetrafluoroborate)]$_2$;

π-allyl-nickel-2-dicyclopentylphosphinoethyl-4-pyridine;

[NiCl$_2$, acenaphthyl-bis(4-trifluoromethylphenylimine)];

[NiCl$_2$, glyoxal-bis(2,6-dimethylphenylimine)]; and

[NiCl2, diacetyl-bis(2,6-diisopropylphenylimine)].

13. A catalyst composition according to claim 11, characterized in that the phosphorus-containing ligand is selected from:

phosphines with general formulae:

PR'$_1$R'$_2$R'$_3$ and R'$_1$R'$_2$P-R'-PR'$_1$R'$_2$ in which R'$_1$, R'$_2$ and R'$_3$, which may be identical or different, are alkyl, cycloalkyl, aryl or aralkyl radicals containing 1 to 10 carbon atoms; and phosphites with general formulae:

P(OR"$_1$)(OR"$_2$)(OR"$_3$) and (—O—R"$_5$—O—)P(OR"$_2$)

in which R"$_1$, R"$_2$, R"$_3$ and R"$_5$, which may be identical or different, are aryl or aralkyl radicals.

14. A catalyst composition according to claim 13, characterized in that the phosphine or phosphite carries an amine ammonium, alcohol, carboxylic acid, ester, sulfonate, phosphonium or phosphonate function.

15. A catalyst composition according to claim 14, characterized in that the functional phosphine is selected from 2-dicyclopentylphosphinoethyl-4-pyridine, 2-dicyclopentylphosphinoethyl-2-pyridine, 2-diisobutylphosphinoethyl-4-pyridine, 2-diisopropylphosphinoethyl-4-pyridine and their pyridine quaternization derivatives; 2-dicyclopentylphosphinoethyl-N-imidazole, 2-diisopropylphosphinoethyl-N-imidazole, 2-diisobutylphosphinoethyl-N-imidazole and their imidazole quaternization derivatives.

16. A catalyst composition according to claim 11, characterized in that the nitrogen-containing ligand has general formula:

$$R^1-N=CR_2-CR_3=N-R_4$$

in which $R_1$ and $R_4$, which may he identical or different, represent a hydrocarbyl group containing 1 to 12 carbon atoms, for example an alkyl group, a saturated or unsaturated group, a cycloalkyl or aromatic, aryl or aralkyl group, containing 1 to 12 carbon atoms, and $R_2$ and $R_3$, which may be identical or different, each represent hydrogen or a hydrocarbyl residue defined as for $R_1$ and $R_4$.

17. A catalyst composition according to claim 8, characterized in that the aluminoxane is selected from methyl aluminoxane, ethyl aluminoxane, isobutyl aluminoxane and tert-butyl aluminoxane, optionally containing free or complexed trialkylaluminum.

18. A catalyst composition for dimerizing, co-dimerizing and oligomerizing olefins according to claim 1, essentially free of alkyl aluminum dihalides.

19. A process for dimerizing or co-dimerizing or oligomerizing olefins using a catalyst composition according to claim 1, characterized in that an olefin selected from ethylene, propylene, n-butenes and n-pentenes used alone or as a mixture, is dimerized, co-dimerized or oligomerized.

20. A process for dimerizing or co-dimerizing or oligomerizing olefins according to claim 19, characterized in that the olefin is contained in a cut from catalytic cracking or from steam cracking.

21. A process for dimerizing or co-dimerizing or oligomerizing olefins according to claim 19, characterized in that the reaction is carried out in a closed, semi-open or continuous system, with one or more reaction stages, with vigorous stirring, at a temperature of −40° C. to +70° C. and at a pressure from atmospheric pressure to 20 MPa.

22. A process for dimerizing or co-dimerizing or oligomerizing olefins according to claim 21, characterized in that the reaction products and the unreacted reactant or reactants are separated from the catalytic system by decanting then fractionating.

23. A process for dimerizing or co-dimerizing or oligomerizing olefins using a catalyst composition according to claim 17, characterized in that an olefin selected from ethylene, propylene, n-butenes and n-pentenes used alone or as a mixture, is dimerized, co-dimerized or oligomerized.

24. A process for dimerizing or co-dimerizing or oligomerizing olefins using a catalyst composition according to claim 18, characterized in that an olefin selected from ethylene, propylene, n-butenes and n-pentenes used alone or as a mixture, is dimerized, co-dimerized or oligomerized.

* * * * *

UNITED STATES PATENT AND TRADEMARK OFFICE
CERTIFICATE OF CORRECTION

PATENT NO.    : 6,911,410 B2
DATED         : June 28, 2005
INVENTOR(S)   : Vincent Lecocq et al.

It is certified that error appears in the above-identified patent and that said Letters Patent is hereby corrected as shown below:

Column 7,
Line 12, "alkylaluininoxanes" should read -- alkylaluminoxanes --.
Line 25, "1:1." should read -- 1:1 --.
Line 35, "(cycloocta-3,7-triene)" should read -- (cycloocta-1,3,7-triene --.

Column 8,
Line 2, "amine" should read -- amine, --.

Signed and Sealed this

Eighth Day of November, 2005

JON W. DUDAS
*Director of the United States Patent and Trademark Office*